United States Patent [19]

Desmurs

[11] Patent Number: 4,503,239

[45] Date of Patent: Mar. 5, 1985

[54] PROCESS FOR THE PREPARATION OF ETHYLENIC HALOGENOACETALS

[75] Inventor: Jean Desmurs, Lyons, France

[73] Assignee: Rhone-Poulenc Sante, Courbevoie, France

[21] Appl. No.: 450,447

[22] Filed: Dec. 16, 1982

[30] Foreign Application Priority Data

Dec. 18, 1981 [FR] France .................. 81 23685

[51] Int. Cl.³ .......................................... C07D 319/06
[52] U.S. Cl. .................................... 549/369; 549/455; 568/459; 568/596
[58] Field of Search ................ 549/455, 369; 568/459, 568/596

[56] References Cited

U.S. PATENT DOCUMENTS

| | | | |
|---|---|---|---|
| 3,160,636 | 12/1964 | Schmerling | 549/369 |
| 3,760,004 | 9/1973 | Freyschlag et al. | 568/596 |
| 4,100,201 | 7/1978 | Decor | 549/369 |
| 4,335,047 | 6/1982 | Jaedicke et al. | 549/369 |

FOREIGN PATENT DOCUMENTS 625178  8/1961  Canada .................. 568/459

*Primary Examiner*—Ethel G. Love
*Attorney, Agent, or Firm*—Stevens, Davis, Miller & Mosher

[57] ABSTRACT

Process for the preparation of halogenoacetals of the general formula:

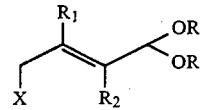

wherein X represents chlorine or bromine, the symbols R each represent a linear or branched alkyl radical (1 to 6 carbon atoms) or together form a linear or branched alkylene radical (2 to 6 carbon atoms), and the symbols $R_1$ and $R_2$, which are identical or different, represent a hydrogen atom or an alkyl radical (1 to 6 carbon atoms), by reaction of chlorine or bromine with a $\beta,\gamma$-ethylenic aldehyde, in the presence of a tertiary amide, followed by reaction with a primary or secondary aliphatic alcohol, a diol (preferably a glycol) or an alkyl orthoformate.

7 Claims, No Drawings

PROCESS FOR THE PREPARATION OF ETHYLENIC HALOGENOACETALS

The present invention relates to a new process for the preparation of ethylenic halogenoacetals of tthe general formula:

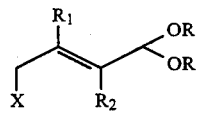

in which: X represents a halogen atoms chosen from chlorine and bromine, the symbols $R_1$ and $R_2$, which aree identical or different, represent a hydrogen atom or a linear or branched alkyl radical containing 1 to 6 carbon atoms, and the symbols R each represent a linear or branched alkyl radical containing 1 to 6 carbon atoms, or together form a linear or branched alkylene radical containing 2 to 6 carbon atoms.

The ethylenic halogenoacetals of the general formula (I) are organic compounds which are particularly useful in organic synthesis. They can be used to introduce an $\alpha,\beta$-ethylenic aldehyde unit into a monoenic or polyenic radical by reaction with an ethylenic or polyenic sulphone in the presence of an alkaline agent, by the process described in Belgian Pat. No. 794,872, the sulphone resulting from this condensation then being desulphonated with the formation of an additional double bond.

In particular, retinal (aldehyde of vitamin A) can be prepared by reaction of 4-bromo-3-methyl-1,1-diethoxybut-2-ene with phenyl 5-(2,6,6-trimethylcyclohex-1-enyl)-3-methylpenta-2,4-dienyl sulphone and then desulphonation of the resulting 5-phenylsulphonyl-9-(2,6,6-trimethylcyclohex-1-enyl)-1,1-diethoxy-3,7-dimethylnona-2,6,8-trien-1-al to give retinal.

It is known that $\alpha$-halogenocetals of $\alpha,\beta$-ethylenic aldehydes can be prepared by the halogenoalkylation of a 1-alkoxy-1,3-diene by reaction with an N-halogenosuccinimide in the presence of an alcohol, by the process described by S. M. MAKIN et al., J. Gen. Chem. U.S.S.R., 32, 1,088 (1962). This process has the disadvantage that the starting diethylenic ethers are difficult to obtain; they are generally prepared by treatment of 1,1,3-trialkoxy-3-methylbutane and 1,1-dialkoxy-3-methylbut-2-ene at high temperature in the presence of catalysts (S. M. MAKIN et al., J. Gen. Chem. U.S.S.R. 29, 116 (1959)), these units also being difficult to obtain.

According to Belgian Pat. Nos. 851,779 and 851,780, it is also known to prepare inter alia the products of the general formula (I) by reaction of a halogenating agent, chosen from amongst the halogen cations $Cl^+$, $Br^+$ and $I^+$, either with an ester of the general formula:

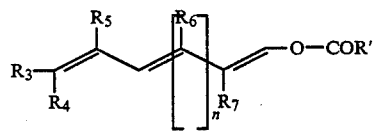

in which R' represents an alkyl radical containing 1 to 6 carbon atoms in a linear or branched chain, $R_3$, $R_4$, $R_5$, $R_6$ and $R_7$, which are identical or different, represent a hydrogen atom or an alkyl radical containing 1 to 6 carbon atoms in a linear or branched chain, or an alkenyl radical which contains 3 to 6 carbon atoms in a linear or branched chain and in which the double bond is in a position other than the 1,2-position, and n is equal to 0, 1, 2, 3 or 4, it being understood that if n is greater than 1, the various symbols $R_6$ can be identical or different, or with an enoxysilane of the general formula:

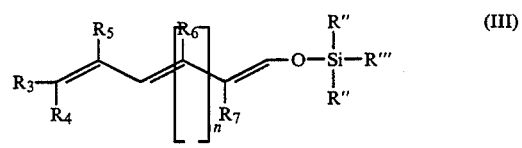

in which $R_3$, $R_4$, $R_5$, $R_6$ and $R_7$ are defined as above, $R''$ represents an alkyl radical containing 1 to 12 carbon atoms in a linear or branched chain, a cycloalkyl radical containing 3 to 6 carbon atoms, a phenyl radical, an alkylphenyl radical in which the alkyl part contains 1 to 6 carbon atoms, or a phenylalkyl radical in which the alkyl part contains 1 to 6 carbon atoms, and $R'''$ is identical to $R''$ or represents a radical of the general formula:

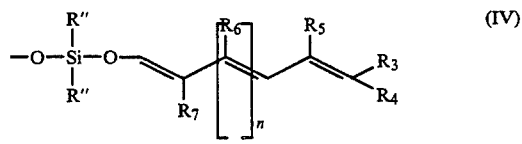

in which $R_3$, $R_4$, $R_5$, $R_6$, $R_7$, n and $R''$ are defined as above, followed by reaction with a primary or secondary aliphatic alcohol or a glycol. Amongst the sources of halogen cations, there may be mentioned, inter alia, the complexes produced by reaction of chlorine, bromine or iodine with dimethylformamide, dimethylacetamide or N-methylpyrrolidone.

The processes known in the prior state of the art have the disadvantage of using expensive reactants, such as isoprenyl acetate or trimethylchlorosilane, to convert the prenal to the halogenoacetal of the general formula (I)

It has now been found that the halogenoacetals of general formula I can be obtained, with good yields, from starting materials which are more readily accessible than those used in the processes known hitherto.

The present invention accordingly provides a process for the preparation of halogenoacetals of the general formula (I) which comprises reacting chlorine or bromine with a $\beta,\gamma$-ethylenic aldehyde of the general formula:

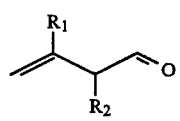

wherein $R_1$ and $R_2$ are as defined above, in the presence of a tertiary amide such as dimethylformamide, dimethylacetamide or N-methylpyrrolidone, to give a halogenoaldehyde of the general formula:

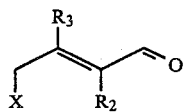

in which X, $R_1$ and $R_2$ are defined as above, and reacting the halogenaldehyde obtained with a primary or secondary aliphatic alcohol containing 1 to 6 carbon atoms, a diol (preferably a glycol) containing 2 to 6 carbon atoms or an alkyl orthoformate, to obtain the ethylenic halogenoacetal of formula I.

In general, to prepare the halogenoaldehyde of the general formula (VI), it suffices to react one molecule of halogen per mol of aldehyde of the general formula V, in which $R_1$ and $R_2$ are defined as above, it being possible, however, for an excess of one or other of these reactants to be used without disadvantage.

Generally, the halogenation of the aldehyde of the general formula (V) is carried out at a temperature of from −40° to 0° C.

The acetalisation of the halogenoaldehyde of the general formula (V) can be carried out:

either by reacting a primary ot secondary aliphatic alcohol, a diol (preferably a glycol) or an alkyl orthoformate, in the presence of a mineral acid such as hydrochloric or hydrobromic acid, with the halogenoaldehyde isolated from the reaction mixture at the end of the halogenation stage, or by adding a primary or seconary aliphatic alcohol, a diol (preferably a glycol) or an alkyl orthoformate to the reaction mixture at the end of the halogenation stage.

The acetalisation is generally carried out at a temperature of from 0° to 50° C.

The ethylenic halogenoacetal of the general formula (I) obtained by the process of the present invention can be isolated from the reaction mixture and purified by applying the usual methods of extraction and purification (distillation, chromatography).

The aldehyde of the general formula (V) can be obtained by known methods. For instance, 3-methylbut-3-enal used as a starting material can be prepared by the method described by J. W. CORNFORTH and F. P. ROSS, Chemical Communications, 1,395 (1970), by the hydrolysis of 1,1-diethoxy-3-methylbut-3-ene, which is obtained by reaction of methallyl chloride with ethyl orthoformate in the presence of magnesium.

In this specification and the accompanying claims it is to be understood that the compounds depicted in formulae I and VI which possess a carbon to carbon double bond may be the cis or trans isomers, or a mixture thereof.

The Examples which follow, which are given without implying a limitation, illustrate how the present invention is put into effect. In the Examples percentages are by weight.

EXAMPLE 1

3-Methylbut-3-enal (6.08 g; 0.0687 mol) and dimethylformamide (80 cc) are introduced into a 500 cc reactor fitted with a stirrer, a condenser and a dip tube making it possible to introduce chlorine, the system having been purged beforehand with a stream of argon. After the mixture has been cooled to −20° C. chlorine gas (4.88 g; 0.0685 mol) is introduced over a period of 70 minutes, entrained by a stream of argon. After the addition of the chlorine has ended, stirring is continued for 40 minutes at a temperature of −20° C. After the temperature has been allowed to rise to about 20° C., the reaction mixture is poured into iced water saturated with sodium chloride (170 cc). After extraction of the mixture with diethyl ether (3×100 cc), the organic phase is washed with water saturated with sodium chloride (50 cc), dried over sodium sulphate and then concentrated to dryness under reduced pressure (20 mm Hg; 2.7 kPa) at 20° C. This givens a yellow oil (10.22 g) which, according to determination by nuclear magnetic resonance, contains 60% of 4-chloro-3-methylbut-2-enal.

The 3-methylbut-3-enal used as the starting material can be prepared in the following manner:

Ethyl orthoformate (792.3 g; 5.353 mols) and magnesium (346.5 g; 14.437 gram atoms) are introduced into a 3 liter reactor fitted with a stirrer, a reflux condenser and a dropping funnel, the system having been purged beforehand with argon. After the reaction mixture has been heated to 60° C., methallyl chloride (8 cc) and methyl iodide (0.1 g) are added. As soon as the reaction starts, the heating is stopped and methallyl chloride (452.7 g; 5.002 mols) is then added so as to keep the temperature at about 60° C. The addition lasts about 14 hours. After cooling to a temperature of the order of 5° C., a saturated solution of ammonium chloride (400 cc) is added without the temperature exceeding 10° C.

After diethyl ether (800 cc) has been added, the inorganic compounds are removed by filtration and washed with diethyl ether (2×1,000 cc). The filtrate and the washings are taken up in water (500 cc) containing oxalic acid (31 g) in order to remove the unreacted ethyl orthoformate. The organic phase is washed with a saturated solution of potassium carbonate (2×50 cc) and is then dried over sodium sulphate. After filtration and concentration to dryness under reduced pressure (200 mm Hg; 27 kPa) at 30° C., a colourless liquid (731 g) is obtained, which is purified by distillation. This gives 95% pure 1,1-diethoxy-3-methylbut-3-ene (b.p.$_{2.13\ kPa}$=57° C.) (646.9 g).

1,1-Diethoxy-3-methylbut-3-ene (199.9 g; 1.2019 mols) is added to a solution of oxalic acid dihydrate (7.6 g) in water (1,000 cc). The suspension is stirred for 6 hours 50 minutes. The mixture is extracted with pentane (5×200 cc). The organic phase is dried over sodium sulphate and concentrated rapidly to dryness under reduced pressure at a temperature below 30° C., so as to remove the traces of oxalic acid. The pentane phase is then taken up for distillation in a 40 cm column with MUTIKNIT packing. This givens 95% pure 3-methylbut-3-en-1-al (b.p.$_{101.3\ kPa}$=93°–93.5° C.) (53.5 g).

EXAMPLE 2

3-Methylbut-3-enal (9.30 g; 0.1009 mol) and dimethylformamide (100 cc), distilled and dried beforehand, are introduced into a 500 cc reactor fitted with a stirrer, a reflux condenser and a dip tube making it possible to introduce chlorine, the system having been purged with argon beforehand. After the solution has been cooled to −20° C., chlorine gas (7.17 g; 0.1007 mol) is introduced over a period of 90 minutes, entrained by a stream of argon.

The stirring is continued for 30 minutes at −20° C. after the addition of the chlorine had ended. The temperature is subsequently allowed to rise to about 20° C. and methanol (300 cc) is then added. The reaction mixture is stirred for 2 hours 45 minutes and is then poured into a solution of sodium bicarbonate (12.7 g) in water (370 cc). The aqueous phase, saturated with sodium chloride, is extracted with diethyl ether (200 cc then 4×100 cc). The organic phase is washed successively with water (2×50 cc) and a saturated solution of sodium bicarbonate (50 cc) and is then dried over sodium sulphate. After filtration, the organic phase is concentrated to dryness under reduced pressure (20 mm Hg; 2.7 kPa). This gives an orange oil (15.93 g) in which (65% of 4-chloro-1,1-dimethoxy-3-methylbut-2-ene, (19.5% of cis isomer and 45.5% of trans isomer), are determined by nuclear magnetic resonance.

The yield of the reaction is 62.4%.

EXAMPLE 3

3-Methylbut-3-enal (12.55 g; 0.136 mol) and dimethylformamide (165 cc), distilled and dried beforehand, are introduced into a 500 cc reactor fitted with a stirrer, a reflux condenser and dip tube making it possible to introduce chlorine, the system having been purged with argon beforehand. After this solution has been cooled to −40° C., chlorine gas (9.68 g; 0.136 mol) is introduced over a period of 1 hour 30 minutes, entrained by a stream of argon. The stirring is continued for 30 minutes after the addition has ended, and the temperature is then allowed to rise to about 20° C. A solution of 2,2-dimethylpropane-1,3-diol (14.61 g; 0.136 mol) in dimethylformamide (30 cc) is then added over a period of 15 minutes. The solution is stirred for 1 hour 15 minutes and is then poured into a solution of sodium bicarbonate (17.1 g) in water (500 cc). Extraction is then carried out with diethyl ether (4×100 cc). The organic phase is washed with water (2×50 cc), dried over sodium sulphate and then concentrated to dryness. This gives an orange liquid (26.9 g) in which 89% of 2-(3-chloro-2-methylprop-1-en-1-yl)-5,5-dimethyl-1,3-dioxane is determined by nuclear magnetic resonance.

EXAMPLE 4

3-Methylbut-3-enal (9.22 g; 0.1 mol) and distilled and dried N-methylpyrrolidone (100 cc) are introduced into a 500 cc reactor fitted with a stirrer, a reflux condenser and a dropping funnel, the system having been purged with argon beforehand. After this solution has been cooled to −10° C., bromine (15.98 g; 0.0999 mol) is added over a period of 1 hour 30 minutes. The stirring is continued for 30 minutes at −10° C. and the temperature is then allowed to rise to about 20° C. Ethanol (300 cc) is then added over a period of 15 minutes. The reaction mixture is stirred for 2 hours 45 minutes and is then poured into a solution of sodium bicarbonate (12.7 g) in water (370 cc). Extraction is carried out with diethyl ether (300 cc, then 2×100 cc). The organic phase is washed with water (2×50 cc) and is then dried over sodium sulphate. After filtration and evaporation of the ether, a brown liquid (15.92 g) is obtained, in which 70% of 4-bromo-1,1-diethoxy-3-methylbut-2-ene is determined by nuclear magnetic resonance.

I claim:

1. A process for the preparation of ethylenic halogenoacetals of the formula:

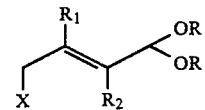

in which X represents a halogen atom selected from chlorine and bromine, the symbols $R_1$ and $R_2$, which are identical or different, represent a hydrogen atom or a linear or branched alkyl radical containing 1 to 6 carbon atoms, and the symbols R each represent a linear or branched alkyl radical containing 1 to 6 carbon atoms, or together form a linear or branched alkylene radical containing 2 to 6 carbon atoms, which comprises reacting chlorine or bromine with a β,γ-ethylenic aldehyde, of the formula:

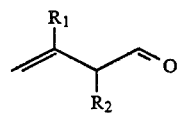

wherein $R_1$ and $R_2$ are defined as above, in the presence of a tertiary amide, to give a halogenoaldehyde of the formula:

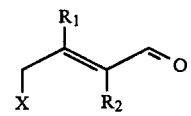

in which X, $R_1$ and $R_2$ are defined as above, and converting the halogenoaldehyde, by reaction with a primary or secondary aliphatic alcohol containing 1 to 6 carbon atoms, a diol containing 2 to 6 carbon atoms, or an alkyl orthoformate, to the ethylenic halogenoacetal.

2. A process according to claim 1 in which the diol is a glycol.

3. A process according to claim 1, wherein the amide is selected from dimethylformamide, dimethylacetamide or N-methylpyrrolidone.

4. A process according to claim 1, wherein the reaction of chlorine or bromine and the β,γ-ethylenic aldehyde is carried out at a temperature of from −40° to 0° C.

5. A process according to claim 1, wherein the conversion of the halogenoaldehyde to the ethylenic halogenoacetal is carried out, at a temperature of from 0° to 50° C.

6. A process according to claim 1, wherein the conversion of the halogenoaldehyde to the ethylenic halogenoacetal is carried out, in the presence of a mineral acid, on the halogenoaldehyde of formula VI isolated from the reaction mixture obtained from the reaction of chlorine or bromine and the β,γ-ethylenic aldehyde.

7. A process according to claim 1, wherein the conversion of the halogenoaldehyde to the ethylenic halogenoacetal is carried out directly on the reaction mixture obtained from the reaction of chlorine or bromine and the β,γ-ethylenic aldehyde.

* * * * *